(12) United States Patent
Benjano

(10) Patent No.: US 12,259,334 B1
(45) Date of Patent: Mar. 25, 2025

(54) METHOD AND APPARATUS FOR ANALYZING A GEMSTONE

(71) Applicant: OGI SYSTEMS LTD., Ramat Gan (IL)

(72) Inventor: Daniel Benjano, Ramat Gan (IL)

(73) Assignee: OGI SYSTEMS LTD., Ramat Gan (IL)

( * ) Notice: Subject to any disclaimer, the term of this patent is extended or adjusted under 35 U.S.C. 154(b) by 0 days.

(21) Appl. No.: 18/887,436

(22) Filed: Sep. 17, 2024

(30) Foreign Application Priority Data

Nov. 27, 2023 (IL) .......................................... 308913

(51) Int. Cl.
*G01N 21/87* (2006.01)

(52) U.S. Cl.
CPC .................................. *G01N 21/87* (2013.01)

(58) Field of Classification Search
CPC ....... G01N 21/3504; G01N 2021/1793; G01N 21/49; G01N 2021/3531; G01N 21/31; G01N 2021/3137; G01N 21/255; G01N 2201/129; G01N 2201/0221; G01N 21/88; G01N 2021/8864; G01N 21/8851; G01N 2021/1795; G01N 21/274; G01N 33/0044; G01N 33/0047; G01N 21/35; G01N 21/3554; G01N 21/3563; G01N 2021/3513; G01N 21/21; G01N 21/87; G01N 2223/618; G01N 23/046; G01N 33/0063; G01N 33/02; G01N 33/025; G01N 1/2273; G01N 2001/021; G01N 2021/258; G01N 2021/6417; G01N 2021/8883; G01N 2021/8887; G01N 21/01; G01N 21/39; G01N 21/553; G01N 21/554; G01N 21/658; G01N 21/66; G01N 21/71; G01N 21/74; G01N 21/95; G01N 2223/628; G01N 2223/646; G01N 2291/0289; G01N 23/203; G01N 25/18; G01N 25/72; G01N 27/129; G01N 27/44721; G01N 29/043; G01N 29/0618; G01N 29/069; G01N 29/225;

(Continued)

(56) References Cited

U.S. PATENT DOCUMENTS 5,118,181 A 6/1992 Yifrach et al.
6,331,708 B2 12/2001 Smith
(Continued)

FOREIGN PATENT DOCUMENTS

CA 2028472 A1 * 4/1991
CA 3029507 A1 * 7/2019 .............. G01J 3/108
(Continued)

OTHER PUBLICATIONS

Breeding, Christopher M., et al. "The 'Type' Classification System of Diamonds and Its Importance in Gemology", Gemological Institute of America (GIA), Gems and Gemology, vol. 2, No. 45, Jun. 2009 (Jun. 2009), pp. 96-111, XP055154336.
(Continued)

*Primary Examiner* — Michael P Stafira
(74) *Attorney, Agent, or Firm* — Tarolli, Sundheim, Covell & Tummino LLP

(57) ABSTRACT

A method, system and apparatus for classifying one or more tested gemstones is disclosed. IR images of a tested gemstone are captured at one or more temperatures and analyzed to thereby classify the gemstone into type or class.

11 Claims, 5 Drawing Sheets

(58) Field of Classification Search
CPC .......... G01N 29/265; G01N 29/4427; G01N 29/4481; G01N 31/223; G01N 33/0062; G01N 33/0073; G01N 33/24; G06V 20/52; G06V 40/10; G06V 2201/034; G06V 20/40; G06V 20/41; G06V 20/20; G06V 20/44; G06V 20/49; G06V 10/82; G06V 10/764; G06V 20/10; G06V 40/174; G06V 10/44; G06V 40/172; G06V 10/945; G06V 20/597; G06V 30/142; G06V 10/143; G06V 10/17; G06V 10/25; G06V 10/462; G06V 40/176; G06V 10/56; G06V 40/1341; G06V 40/1347; G06V 40/1365; G06V 40/1388; G06V 40/1394; G06V 40/14; G06V 40/145; G06V 10/507; G06V 10/469; G06V 10/774; G06V 20/80; G06V 10/147; G06V 10/751; G06V 40/103; G06V 10/454; G06V 10/50; G06V 20/64; G06V 2201/03; G06V 40/171; G06V 40/161; G06V 20/46; G06V 20/48; G06V 20/59; G06V 20/593; G06V 20/647; G06V 40/18; G06V 10/75; G06V 40/20; G06V 10/24; G06V 40/168; G06V 40/28; G06V 10/754; G06V 10/763; G06V 10/806; G06V 20/56; G06V 10/10; G06V 10/16; G06V 10/255; G06V 10/803; G06V 10/96; G06V 20/58; G06V 40/165; G06V 10/811; G06V 10/95; G06V 10/955; G06V 20/00; G06V 20/188; G06V 2201/07; G06V 40/162; G06V 40/166; G06V 40/179; G06V 40/19; G06V 10/85; G06V 20/194; G06V 20/695; G06V 20/698; G06V 40/15; G06V 40/16; G06V 10/267; G06V 10/40; G06V 10/48; G06V 10/58; G06V 10/758; G06V 10/772; G06V 10/80; G06V 40/167; G06V 40/23; G06V 40/45; G06V 10/141; G06V 10/54; G06V 10/62; G06V 10/70; G06V 10/766; G06V 20/66; G06V 20/68; G06T 7/0012; G06T 2207/10016; G06T 2207/10048; G06T 2207/20084; G06T 7/70; G06T 2207/30004; G06T 11/001; G06T 2207/20081; G06T 2207/10028; G06T 7/20; G06T 2207/30088; G06T 2207/30101; G06T 19/20; G06T 7/90; G06T 2207/30201; G06T 7/42; G06T 2207/10024; G06T 7/0014; G06T 2219/2012; G06T 11/60; G06T 7/73; G06T 7/0002; G06T 19/006; G06T 2207/30244; G06T 7/0004; G06T 1/20; G06T 7/001; G06T 11/206; G06T 17/00; G06T 2207/30108; G06T 2215/16; G06T 3/18; G06T 5/50; G06T 7/13; G06T 7/55; G06T 7/97; G06T 15/205; G06T 2207/30181; G06T 7/62; G06T 2207/10012; G06T 2207/30252; G06T 5/70; G06T 7/521; G06T 2219/2016; G06T 7/12; G06T 7/50; G06T 1/00; G06T 2207/20012; G06T 2207/20076; G06T 2207/30041; G06T 2207/30204; G06T 2207/30248; G06T 2207/30261; G06T 3/4038; G06T 5/00; G06T 7/00; G06T 7/136; G06T 7/30; G06T 7/33; G06T 7/344; G06T 7/593; G06T 7/60; G06T 7/77; G06T 11/00; G06T 17/10; G06T 17/20; G06T 2200/24; G06T 2207/10036; G06T 2207/10081; G06T 2207/20221; G06T 2207/30168; G06T 2207/3068; G06T 2210/16; G06T 2210/44; G06T 2219/2021; G06T 3/40; G06T 3/4053; G06T 5/77; G06T 7/80; G06T 2207/10052; G06T 2207/20021; G06T 2207/30144; G06T 2207/30232; G06T 3/08; G06T 5/20; G06T 7/194; G06T 7/557; G06T 2207/10032; G06T 2207/10064; G06T 2207/10088; G06T 2207/10092; G06T 2207/10132; G06T 2207/20092; G06T 2207/20104; G06T 2207/30016; G06T 2207/30128; G06T 2207/30192; G06T 5/73; G06T 11/008; G06T 13/00; G06T 2207/20024; G06T 2207/20101; G06T 2207/20182; G06T 2207/20201; G06T 3/02; G06T 5/94; G06T 7/10; G06T 7/75; G06T 2207/10152; G06T 2207/20112; G06T 2207/20224; G06T 2207/30068; G06T 2207/30136; G06T 2207/30176; G06T 2207/30188; G06T 2207/30208; G06T 3/4046; G06T 3/60; G06T 5/40; G06T 5/60; G06T 7/246; G06T 9/00; G06T 9/40

See application file for complete search history.

(56) References Cited

U.S. PATENT DOCUMENTS

| | | | |
|---|---|---|---|
| 8,189,875 B2 * | 5/2012 | Nasser | G06T 7/543 |
| | | | 382/199 |
| 9,176,068 B1 | 11/2015 | Radomyshelsky et al. | |
| 10,309,894 B2 * | 6/2019 | Hsiung | G01N 21/31 |
| 10,684,230 B2 | 6/2020 | Wang et al. | |
| 10,823,680 B2 | 11/2020 | Blank et al. | |
| 11,073,482 B2 | 7/2021 | Zhu et al. | |
| 2005/0117145 A1 | 6/2005 | Altman et al. | |
| 2010/0250201 A1 * | 9/2010 | Sivovolenko | G01B 11/2433 |
| | | | 703/2 |
| 2018/0238811 A1 * | 8/2018 | Tam | G01N 21/87 |
| 2021/0003510 A1 | 1/2021 | Raichelgauz et al. | |
| 2023/0027883 A1 | 1/2023 | Lanigan et al. | |

FOREIGN PATENT DOCUMENTS

| | | | | |
|---|---|---|---|---|
| CH | 690627 A5 * | 11/2000 | ......... | G01N 25/4866 |
| CN | 1902474 A * | 1/2007 | ............ | G01N 21/87 |
| CN | 116773453 A | 9/2023 | | |
| EP | 1158293 A3 | 11/2001 | | |
| EP | 3729063 B1 | 10/2020 | | |
| GB | 2278440 A | 11/1994 | | |
| JP | H10505160 A * | 5/1998 | | |
| WO | 1994020837 A1 | 9/1994 | | |
| WO | 1995020152 A1 | 7/1995 | | |
| WO | 1996007895 A1 | 3/1996 | | |
| WO | 2002006797 A1 | 1/2002 | | |
| WO | 2003023382 A1 | 3/2003 | | |
| WO | WO-2005052540 A2 * | 6/2005 | ............ | G01N 21/87 |
| WO | WO-2015082985 A1 * | 6/2015 | ............ | G01N 21/87 |
| WO | 2015127990 A1 | 9/2015 | | |
| WO | 2017208053 A1 | 12/2017 | | |
| WO | 2020044326 A1 | 3/2020 | | |
| WO | 2021023211 A1 | 2/2021 | | |
| WO | 2021140124 A1 | 7/2021 | | |
| WO | 2021140128 A1 | 7/2021 | | |

(56) References Cited

OTHER PUBLICATIONS

Green, Ben L., et al. "Diamond Spectroscopy, Defect Centers, Color, and Treatments", Reviews in Mineralogy and Geochemistry, vol. 88, No. 1, Jul. 2022 (Jul. 2022), pp. 637-688, XP093161842.

* cited by examiner

METHOD AND APPARATUS FOR ANALYZING A GEMSTONE

RELATED APPLICATIONS

This application is a U.S. Non-Provisional Application, claiming priority to Israeli Application No. 308913 filed 27 Nov. 2023, the entirety of which is hereby incorporated herein by reference.

TECHNOLOGICAL FIELD

The present disclosure is in the field of identifying gemstones, particularly diamonds.

BACKGROUND ART

In general, the composition and crystal structure of a synthetic diamond is identical with that of a geologically formed natural diamond. However, synthetic diamonds are less valuable than synthetic, it is not unusual for jewelry manufacturers to use synthetic diamonds instead of natural ones, particularly in jewelry pieces that includes a plurality of small diamonds where it is especially difficult to distinguish between those that are authentic and those that are not.

In addition to synthetic diamonds, numerous other cheap materials are often used as imitation diamonds in jewelry, e.g., cubic zirconia, moissanite, glass, crystals, rhinestones and white sapphires. It can be difficult to distinguish between natural diamonds and synthetic or imitation diamonds when used in jewelry.

Various optical techniques have been developed for distinguishing synthetic diamonds from natural diamonds. These include instruments based on ultraviolet and infrared (IR) imaging techniques. These techniques irradiate a tested gemstone with ultraviolet and/or IR radiation and analyze the spectrum of the reflected radiation from the tested gemstone to determine signatures of natural and/or synthetic diamonds. For example, in some cases, various defects or impurities in the crystal structure of a synthetic diamond may result in optical properties that may be measurable to distinguish the synthetic diamond from a natural diamond.

Other methods may include a testing probe for determining a thermal conductivity and/or the electrical conductivity of the tested gemstone in order to classify the gemstone by its physical properties.

References considered to be relevant as background to the presently disclosed subject matter are listed below:
U.S. Pat. No. 11,073,482B2
WO1996007895A1
U.S. Pat. No. 5,118,181A
EP3729063B1
U.S. Pat. No. 10,823,680B2
WO2003023382A1
WO2015127990A1
WO2002006797A1
WO2021140124A1
WO2021023211A1
CN116773453A
WO2021140128A1
WO2020044326A1
U.S. Pat. No. 10,684,230B2
WO2017208053A1
U.S. Pat. No. 9,176,068B1
EP1158293A3
U.S. Pat. No. 6,331,708B2
WO1995020152A1
WO1994020837A1

Acknowledgement of the above references herein is not to be inferred as meaning that these are in any way relevant to the patentability of the presently disclosed subject matter.

GENERAL DESCRIPTION

The term "gemstone", used herein refers to any one of a variety of ornamental precious stones including, but not limited to diamonds. It also refers to gemstones both in isolation (namely not yet set in a jewelry piece); as well as when set in a piece of jewelry, that may contain several gemstones, ranging in quantity from a few (single digit number) to several tens and, at times even hundreds of gemstones (e.g. many small ones).

By one embodiment of this disclosure, different kind of gemstones may be identified. In the gemstone industry, gemstones are generally classified into 4 categories: natural diamonds, synthetic or laboratory produced diamonds, variety of colored gemstones and simulant stones that include zirconium, glass-based gems and others. It is often difficult to discern between the different gemstones in standard methods. For example, irradiating simulants with ultraviolet (UV) light, which is the standard method for classifying gemstones, gives a very similar signature as that obtained for natural white diamonds. There is a specific unmet challenge, under existing methods and systems, to discern non-natural gemstones, such as those made out of glass, from natural ones, when set in a piece of jewelry. Also, known methods often fail to distinguish between natural diamonds and such produced synthetically, particularly when set in a piece of jewelry.

It was realized in accordance with embodiments of this disclosure that obtaining IR images of the gemstones at defined temperatures may permit to discern between different gemstones with a higher degree of confidence as compared to existing methods.

Diamonds are classified according to their color into categories known as categories D to Z. All existing methods and systems can classify diamond between category K down to D but fail to discern between diamonds in categories Z to K. Even a trained eye cannot discern between the different categories below K when set in a piece of jewelry. The method/system and apparatus disclosed herein provide a means for discerning between such different categories. In addition, the method and apparatus of this disclosure may be, by some embodiments, be adapted to differentiate between one or more of (i) diamonds of different color classes, (ii) white diamonds of different shades or purity, and (iii) natural diamonds of different colors.

Also, by some embodiments of this disclosure, synthetic diamond of different kind may be classified, for example for the purpose of differentiation between natural less precious and more precious diamonds through their IR image.

According to some embodiments of this disclosure the accuracy of classification and differentiation may be improved if the IR-based imaging is supplemented by a UV-based testing, e.g. of the kind known in the art.

The present disclosure provides a method and apparatus for analyzing a gemstone that is referred to herein as a "tested gemstone". It should however be noted that the present disclosure is not limited to one gemstone and the system and method described herein is also suitable for analyzing a plurality of gemstones simultaneously. A tested gemstone is one that its identity is unknown, or there is an alleged identity, and it is intended to determine, in a manner disclosed herein, whether it has the alleged identity or another. A tested gemstone may, for example, be one indicated to be a natural diamond and may be assayed to determine whether it is, indeed, a natural diamond or a synthetic one or perhaps even an imitation made from another material such as glass or plastic.

In some embodiments of this disclosure the tested gemstone may be tested as such (namely before it is set in a jewelry piece). In other embodiments the tested gemstone may be set in a jewelry piece and the method, system and apparatus may be employed to assay the tested gemstone within the jewelry piece.

In some embodiments there may be a plurality of tested gemstones tested in parallel, for example a plurality of individual tested gemstones spread out on a test plate or in a testing zone in the apparatus or a plurality of tested gemstones set in a jewelry piece. Each tested gemstone may be analyzed and classified. It is possible, in some embodiments, to assay a plurality of jewelry pieces at the same time.

It was observed in accordance with this disclosure, that by analyzing captured IR images of the tested gemstone at one or more temperatures, optionally comparing images to reference images, gemstones can be properly classified with a high degree of accuracy. Use may also be made with AI-based algorithms for the determination the identity of one or more gemstones, pre-trained by exposure to many IR images of known gemstones, both in isolation as well set in different pieces of jewelry. However, it should be understood, that such an algorithm, while pre-trained, may also undergo continued training when used in practice and the algorithm may undergo continued refinement when in use.

In some embodiments of this disclosure the IR analysis may be combined with one made with UV images captured under UV irradiation. Typically, based on a measure of correlation between images of the tested gemstone and reference images of known gemstones, it is possible to determine whether the tested gemstone is an actual gemstone or an imitation. In addition, the method, system or apparatus may determine the class to which the gemstone belongs. For example, to determine whether a diamond set in a jewelry piece is a genuine or synthetic diamond.

It should be noted that the term "images" or "IR images" or "UV images" used through this disclosure should be interpreted broadly covering static/discrete images (e.g., obtained at selected temperatures or time intervals) and/or a continuous stream of images (e.g., video) or any combination thereof. Accordingly, even is not specifically stated any reference to a sensor (whether one intended for capturing IR images or one intended for capturing images in the UV spectrum) in the flowing general description or detailed description, even if not specifically stated, is intended to denote a sensor that can capture discrete images, a continuous stream of images, e.g. images captured in a distinct temporal sequence, such as a video stream, or a combination of discrete images and a continuous stream of images.

The measure of correlation between images of the tested gemstone and reference images of known gemstones may be a defined spectrum, a change in the image or a defined spectral fraction thereof over time upon heating or cooling; and in general, any measure that can be recorded by an IR sensor.

By way of example, where the tested gemstone is not a genuine precious stone, such as a diamond, but rather the tested gemstone may be cubic zirconia, glass, crystals, or rhinestone that resemble diamonds in general appearance, an output of the method, system or apparatus may give rise to such a determination. Alternatively, the method, system or apparatus may lead to the determination of the exact nature of the tested gemstone, namely it may determine the type or defined class of the gemstone, e.g., natural diamonds, synthetic diamonds, white sapphires or moissanites. Distinguishing between natural diamonds and synthetic or imitation diamonds is one embodiment of the method, system or apparatus of this disclosure.

Provided by one aspect of this disclosure is a method for classifying one or more tested gemstones. It comprises capturing IR images of the tested gemstone at one or more, typically two or more, defined temperatures. The defined temperature may include temperatures higher than ambient temperature in which case the tested gemstone is heated to one or more examination temperature and image may then be captured. The defined temperature may also be a temperature lower than ambient temperature in which case the tested gemstone is cooled to one or more examination temperatures and image may then be captured. The examination temperature may also include a combination of one or more examination temperatures that are achieved through heating, one or more examination temperatures that are achieved through cooling, or a combination of the two. The present disclosure is not limited by the type of examination temperature and any combination of temperature, including such chosen according to a pre-defined examination scheme or at random.

In some embodiments of this disclosure, a plurality of IR images are continuously captured, e.g. at defined intervals, during cooling or heating, and not only at defined temperature. Typically, at the same time temperature readings are obtained to permit correlation between the recorded temperatures and the captured IR images. As it may, at times, be difficult to obtain an accurate temperature reading of each tested gemstone, the temperature reading may be obtained from a reference element in the vicinity of the one or more gemstones, e.g. from the plate or panel on which the one or more tested gemstones, or the jewelry piece on which they are set, is positioned. Where the temperature is controlled by a heating or cooling air or another gas, the temperature reading may be that of such a gas. When gas is used for heating or cooling, the change in temperature may be made to be gradual such to ensure that the temperature of the one or more tested gemstones is approximately that of the temperature-controlling gas.

One or more IR image of the one or more tested gemstone in at least one specific temperature received in a processor, is analyzed, and based on the analysis, each of the one or more tested gemstone is classified to obtain a respective classification descriptor that may be outputted to a user interface, e.g., a display of an apparatus of a certifying body, transmitted to a customer device, recorded in a database, etc.

The analysis may comprise comparing the one or more infrared images to respective reference infrared images of gemstones belonging to a defined class and associated with the at least one certain temperature, and determining whether the tested gemstone belongs to the defined class based on a first measure of correlation of the one or more infrared images to the respective reference infrared images. As noted above, use may also be made of pre-trained, AI-based algorithms/model. The AI model may be pre-trained to analyze IR images of gemstones and distinguish between types of gemstones, and between classes of the same type, e.g. between different diamond categories, for gemstones in isolation (i.e. not set in a piece of jewelry) as well as for gemstones within a piece of jewelry. The pre-trained AI model may be one trained to distinguish gemstones based on discrete IR images, based on a sequence of images, e.g. a video stream, or a combination of both discrete and a steam of images (e.g. video).

The classification descriptor may be a numerical value or set of numerical values that are determined on the basis of IR spectral analysis, change in the spectral analysis at different temperatures, the spatial spectral distribution in a gemstone at one or more defined temperatures, etc. It may also be a graphical representation of the stone, for example using false colors or shadings to identify gemstones belonging to a defined class of precious or non-precious stones, etc. This disclosure is mot limited by the type of display or the manner in which the information is presented.

Provided by another aspect of this disclosure is a system for analyzing one or more tested gemstones/model. The AI model may be pre-trained to analyze IR images of gemstones and distinguish between types of gemstones, and between classes of the same type, e.g. between different diamond categories, for gemstones in isolation (i.e. not set in a piece of jewelry) as well as for gemstones within a piece of jewelry. The pre-trained AI model may be one trained to distinguish gemstones based on discrete IR images, based on a sequence of images, e.g. a video stream, or a combination of both discrete and a steam of images (e.g. video).

The system/apparatus comprises one or more IR sensors configured to obtain discrete or a continuous stream of IR images of a tested gemstone. This means, for example, that the one or more sensors may be positioned in such a manner to permit them to capture images of the tested gemstone once placed on a test plate or in a testing zone in the system/apparatus. The IR sensor may be an IR charged-coupled device (CCD), with or without a lens, a camera configured for capturing still images or a video stream or any other suitable device for capturing IR images. In other embodiments the system/apparatus comprises two or more IR sensors; for example, each configured to capture an image of the tested gemstone from a different angle. The system/apparatus further comprises a control unit that has, in the case of the system, a processing utility that is communicatively linked to the one or more sensors, or in the case of the apparatus may comprise such a processor or be communicatively coupled to both the one or more sensors and also communicatively coupled to an external processing utility. The processing utility may comprise one or more processors configured for receiving and analyzing data representative of the IR images captured by the one or more IR sensors, to obtain a respective classification descriptor for each of the one or more tested gemstones. By some other embodiments, an internal processor of the system/apparatus may be communicatively linked to an external processor, e.g. an AI-based processing utility in an external computer or server system accessible through a wired or wireless communication link or a server in the 'cloud' and accessible through the internet. By said other embodiments, the processing of the images may a distributed processing, partially being performed in the internal processor and partially by the external processor. This is of particular advantage in an AI-based processing in which the respective algorithm may continuously improve through ongoing training.

The control unit may also comprise or being communicatively couplable to an output utility for outputting said classification descriptors. The output utility may comprise a display or a coupling circuitry for coupling and delivering the classification descriptor to one or more other systems/apparatuses, e.g., an external computer, a remote server, an external display, etc. In some embodiments the system/apparatus comprises a temperature control utility configured for controlling heat of the tested gemstone. The system/apparatus may also comprise one or more temperature sensing elements for sensing the temperature of the tested gemstone and feedback it to the temperature control utility. The temperature control utility may, for example, comprise one or more heating plates or another device that is configured to hold the tested gemstone or a jewelry piece comprising it and heat it through contact, a device configured for convection heating, a device comprising one or more radiators for radiating heat onto the gemstone, or any other suitable heating device.

Some embodiments will now be described-applicable to all aspects of this disclosure.

In some embodiments, the processor is configured to process IR images of the tested gemstones, captured by the one or more sensor, at one or more defined temperatures and output, based thereon, for each of the one or more tested gemstones a respective classification descriptor.

The temperature control by some embodiments may comprise heating the tested gemstone and permitting it to cool and while it is cooled capturing and analyzing one or more IR images at defined temperatures.

In some embodiments the tested gemstones may be subject to a gradual heating or cooling process while capturing and analyzing one or more IR images during such change, typically at defined temperatures.

In some embodiments IR images are captured at defined time intervals during heating or cooling and the tested gemstone classification is based, at least partially, on the gemstones temporal IR profile. The temporal profile may, by some embodiments, be analyzed to discern between different gemstones, even without an accurate reading of temperature, for example by pre-trained AI-based systems, as defined above. In some embodiments the temperature may be abruptly raised or cooled, and such temporal analysis of the IR images may be analyzed based on expected temporal temperature change of different gemstones, e.g. by a pre-trained AI-based system.

In some embodiments, IR images are captured while heating the gemstones, in some embodiments while cooling them and in others both during heating and during cooling.

In some embodiments, the processor is configured to compare said IR images to reference IR images of gemstones belonging to a defined class and determine for each of the one or more tested gemstones whether the tested gemstone belongs to the defined class based on a first measure of correlation of said IR images to said reference IR images. The respective classification descriptor for each of the one or more tested gemstones may comprise an indication of the measure of correlation, e.g., an indication of the level of confidence, e.g. in a percentage points, that the tested gemstone (associated with its respective classification descriptor) is of a defined nature; or may be a positive "yes" or "no" indicator based on meeting a certain pre-defined threshold correlation value that the tested gemstone belongs to a defined class, such as a natural diamond.

In some embodiments, several IR images at each temperature are captured and the analysis may comprise deriving a combined image, which may be an average image (or any other statistical or other combination of these images) of the plurality of images, and the combined image or data representative thereof may then be compared to a reference image or data representative thereof. The reference image may also be corresponding combined image of many reference images. The term "image" as used herein should, thus, be understood to also mean an average of two or more images, a representative image obtained by combining individual images obtained under similar conditions in any other way, or data representative thereof.

In some embodiments, there may be different reference images for different shapes or sizes of precious stones, for stones that are set in a jewelry piece or are free, etc. Where the analysis is AI-based, such reference images may those used for training the AI algorithm.

In some embodiments, the system/apparatus comprises a UV radiation source configured to irradiate the one or more tested gemstones at one or more UV wavelengths; and a UV sensor configured to capture UV images of the one or more tested gemstones at one or more UV wavelengths. The processor in such embodiments may be further configured to analyze said UV images and said IR images, and classify each of the one or more tested gemstone, based on a such a combined analysis.

In some embodiments, to analyze said UV images and said IR images, the processor may be further configured to: compare said IR images to reference IR images of gemstones belonging to a defined class, compare said UV images to reference UV images of gemstones belonging to the defined class, and determine whether a certain tested gemstone belongs to the defined class based on a combination of the first measure of correlation of said IR images to said reference IR images and a second measure of correlation of said UV images to said reference UV images. Such comparison may also be AI-based utilizing an AI model pre-trained to analyze UV images of gemstones and distinguish between types of gemstones, and between classes of the same type, e.g. between different diamond categories, for gemstones in isolation (i.e. not set in a piece of jewelry) as well as for gemstones within a piece of jewelry. The pre-trained AI model may be one trained to distinguish gemstones based on discrete images, based on a sequence of images, e.g. a video stream, or a combination of both discrete and a steam of images (e.g. video).

The AI system may also be trained to make the analysis on a combination of IR and UV images.

In some embodiments, the processor is configured to analyze the tested gemstone and determine whether the tested gemstone is a precious stone. The precious stone may be a diamond and the processor may be further configured to determine whether the tested gemstone is a natural or synthetic diamond.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION

The following figures are provided to exemplify embodiments of the present disclosure. The disclosure herein is not limited to the below-described embodiments.

Figure 1A:
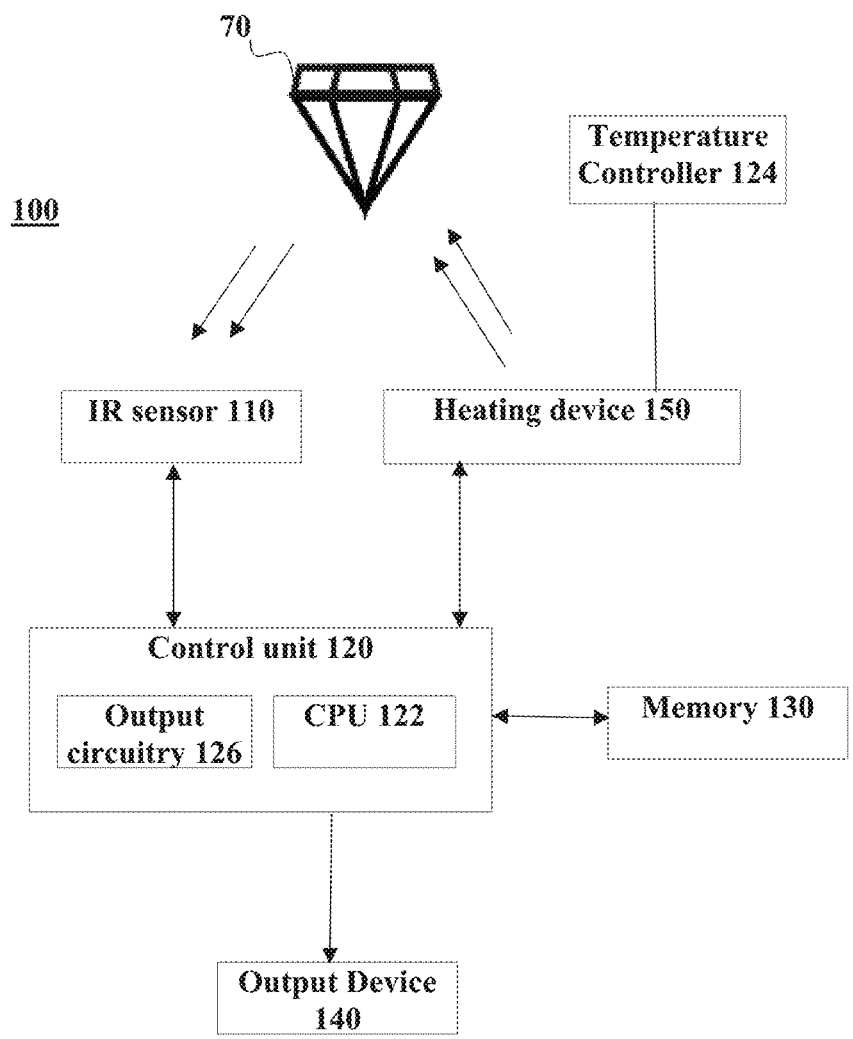
FIG. 1A shows a block diagram of an apparatus for analyzing a tested gemstone, according to some embodiments of the present disclosure.

Reference is made to FIG. 1A, which shows a block diagram of an a system/apparatus 100 for analyzing one or more tested gemstone 70, according to some embodiments of the present disclosure. In this non-limiting example only one such tested gemstone 70 is shown. System/apparatus 100 comprised an IR sensor unit 110, a control unit 120, with processor 122, a temperature controller 124 and an output circuitry 126, a memory 130 (which may be part of the controller or an external device) and an output device 140.

IR sensor unit 110 comprises one or more IR image capturing elements (e.g., an IR or thermal imaging stills or video camera, or any other suitable sensor). Sensor unit 110 may capture IR images of a tested gemstone 70 at one or more defined temperatures. Heating device 150, through control by the temperature controller 124, operated to heat the tested gemstone 70. Heating device 150 may be a plate or another device that is configured to hold the tested gemstone or a jewelry piece comprising it and heat it through contact heat, a convection heater, laser heating, heated fluid, or any other suitable heat source that can operate to increase the tested gemstone's temperature.

It should be noted that In other embodiments, rather than heating, the tested gemstone 70 is cooled and IR images may be captured during cooling or at defined, cooled, temperatures. The colling option may be provided in addition or in the alternative to heating device.

One or more temperature sensors may be provided in system/apparatus 100 for measuring temperature of the gemstone 70 and generate data indicative thereof. The temperature controller 124 can be configured to use the measured data for operating the heating device 150 (or the cooling device in the case of the cooling embodiment) based thereon, e.g., until the gemstone 70 is heated or cooled to a desired/required temperature.

Control unit 120 may be configured, through processor 122, to analyze captured images in accordance with various temperature variation schemes/profiles. For example, control unit 120 can analyze captured images at gradually increasing temperatures of the gemstone 70 and thereafter analyze captured images at gradually decreasing temperatures after initially heating the gemstone, e.g., heating it to 120 degrees Celsius and then permitting it to cool to room temperature.

Processor 122 is configured to record and analyze at least one IR image of tested gemstone 70 for each of at least one defined temperature. It typically records a plurality of images at each of a plurality of temperatures/temperature ranges. The IR images may be stored in memory 130. Processor 122 analyzes said IR images and classifies tested gemstone 70 based on the analysis. Processor 122 may compare said IR images to reference IR images of gemstones belonging to a defined class, stored in and retrieved from memory 130. Alternatively, processor 122 may run an AI algorithm that was trained on known gemstone images at defined temperatures, temporal changes of images of known gemstones during temperature change, etc. Generally, while the description below describes the analysis of the tested gemstone by comparing images to reference images, it should be understood that such analysis may also be done using an AI algorithm pre-trained with such reference images, as generally described above. It should also be noted that such AI system may also be trained to utilize a combination of IR and UV imaging for gemstone classification.

For at least one defined temperature of the one or more defined temperature/temperature range, processor 122 may compare the at least one IR image recorded at the at least one defined temperature to at least one reference IR image of gemstones belonging to a defined class recorded at the same temperature. Processor 122 can determine whether tested gemstone 70 belongs to the defined class based on a first measure of correlation of said at least one IR image to said at least one reference IR image.

For example, in some embodiments processor 122 may compare at least one IR image recorded when the gemstone 70 is heated to a certain temperature/temperature range and compare this at least one IR image to a at least one respective reference IR image of gemstones belonging to a defined class recorded at this certain temperature/temperature range. Additionally, or alternatively, processor 122 may compare at least one IR image recorded when the gemstone 70 is cooled (after being heated) to a certain second temperature/temperature range and compare this at least one IR image to a at least one second reference IR image of gemstones belonging to a defined class recorded at this certain temperature/temperature range.

The first measure of correlation of said IR images to said reference IR images may be indicative of a number of defined features shared between said IR images and said reference IR images. For example, the defined features may be spectral components in the IR spectrum (between 780 nm and 0.1 nm) or color coded heat maps. The defined features may be a spatial spectral distribution at a defined temperature or a temperature-related change at different temperatures. The measure of correlation of said IR images to said reference IR images indicating that the number of defined features shared between said IR images and said reference IR images may be such so as to exceed a defined threshold. The defined threshold may, for example, be determined by a machine learning model trained on said reference IR images.

Figure 1B:
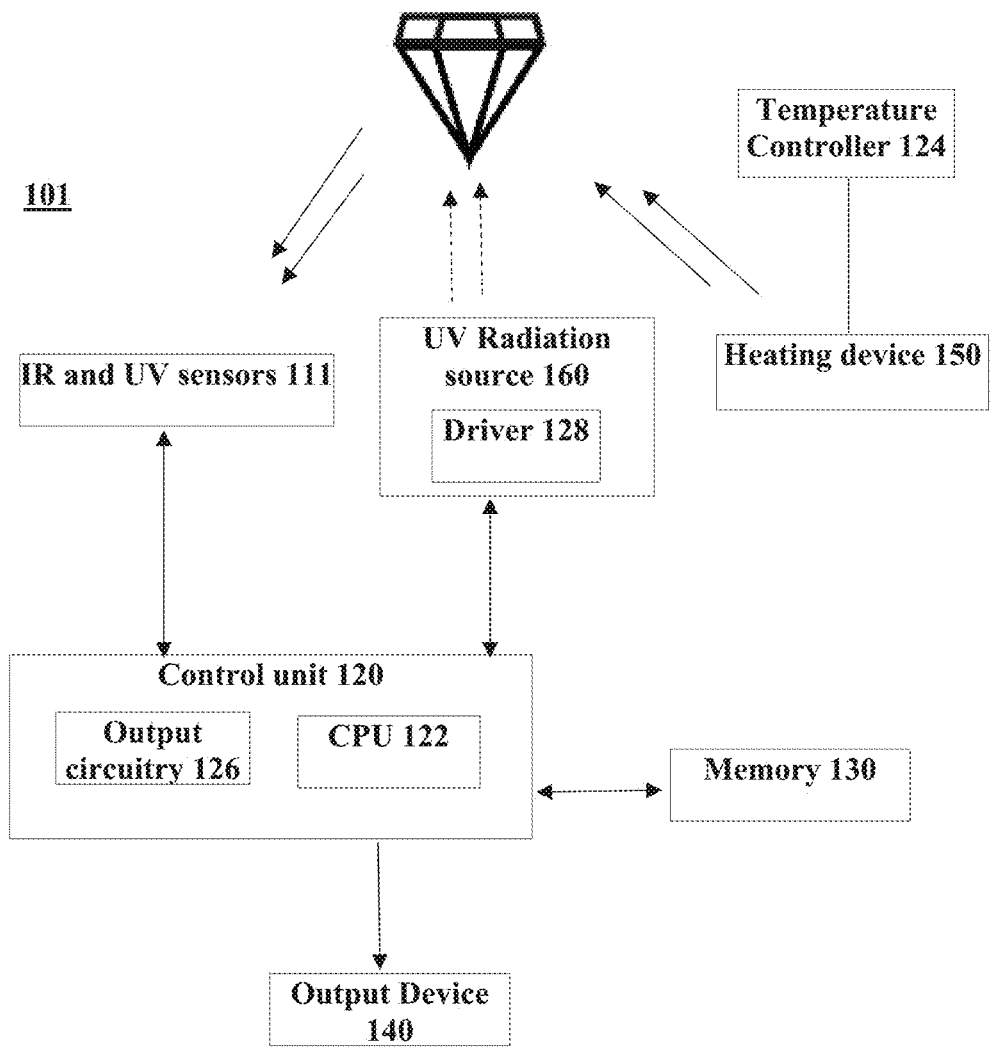
FIG. 1B shows a block diagram of the apparatus for analyzing the tested gemstone including an UV radiation source, according to some embodiments of the present disclosure.

Reference is also made to FIG. 1B, which shows a block diagram of system/apparatus 101 for analyzing tested gemstone 70 with a UV-based analysis in addition to the IR-based one, according to some embodiments of the present disclosure.

System/apparatus 101, as seen in FIG. 1B has an UV radiation source 160, an added driver 128 for driving the UV radiation source 160 and has a sensor unit 111 that includes both IR and UV image sensors. The UV and IR image sensor elements may be configured in one sensing device or the UV sensing elements and the IR sensing elements may be configured in separate devices. Other elements are the same as those described in reference to FIG. 1A.

UV radiation source 160 can emit radiation with wavelengths in the UV spectrum (e.g., UV lamp, UV laser, or any other suitable UV radiation source). For example, UV radiation source 160 may emit radiation with wavelengths in the range of 100-400 nm. Control unit 120 may control UV radiation source 160 to irradiate tested gemstone 70 at one or more UV wavelengths. For example, the one or more UV wavelengths may include one or more wavelengths in the ranges of 100-280 nm and one or more others in the range of 315-400 nm.

The IR and the UV images may be recorded at different operational modes of the system/apparatus 101, one in which the gemstone is heated by temperature control unit 150 and the other in which the gemstone is irradiated by radiation source 160. In other embodiments, both these measurements may be combined and the UV irradiation, which does not interfere with the recording of IR images at different temperatures, may be irradiated and the images thereof recorded, while recording the IR images at different temperatures.

Processor 122 is configured to analyze said UV images and said IR images and classify tested gemstone 70 based on the analysis. Processor 122 compares said UV images to reference UV images of gemstones belonging to the defined class, stored in and retrievable from memory 130. Processor 122 determines whether tested gemstone 70 belongs to the defined class based on a first measure of correlation of said IR images to said reference IR images and a second measure of correlation of said UV images to said reference UV images.

The first measure of correlation of said IR images to said reference IR images may be indicative of the number of defined features shared between said IR images and said reference IR images (e.g., as described herein above). The second measure of correlation of said UV images to said reference UV images may be indicative of a number of defined features shared between said UV images and said reference UV images. For example, the defined features may be spectral components in the UV spectrum (between 100-400 nm). The addition of the analysis of UV images, which may be carried out as known per se, may have an effect of increasing accuracy of determining the nature of the tested gemstone 70.

Control unit 120 of system 100 or 101 may display results of analyzing tested gemstone 70 on output device 140, driven by the output circuitry 126. Output device 140 may be a computer display or any other suitable output device.

To facilitate understanding, in all the figures, the same reference numbers are used to identify functionally similar elements/blocks in different embodiments of the System/apparatus of the present disclosure.

Figure 2:
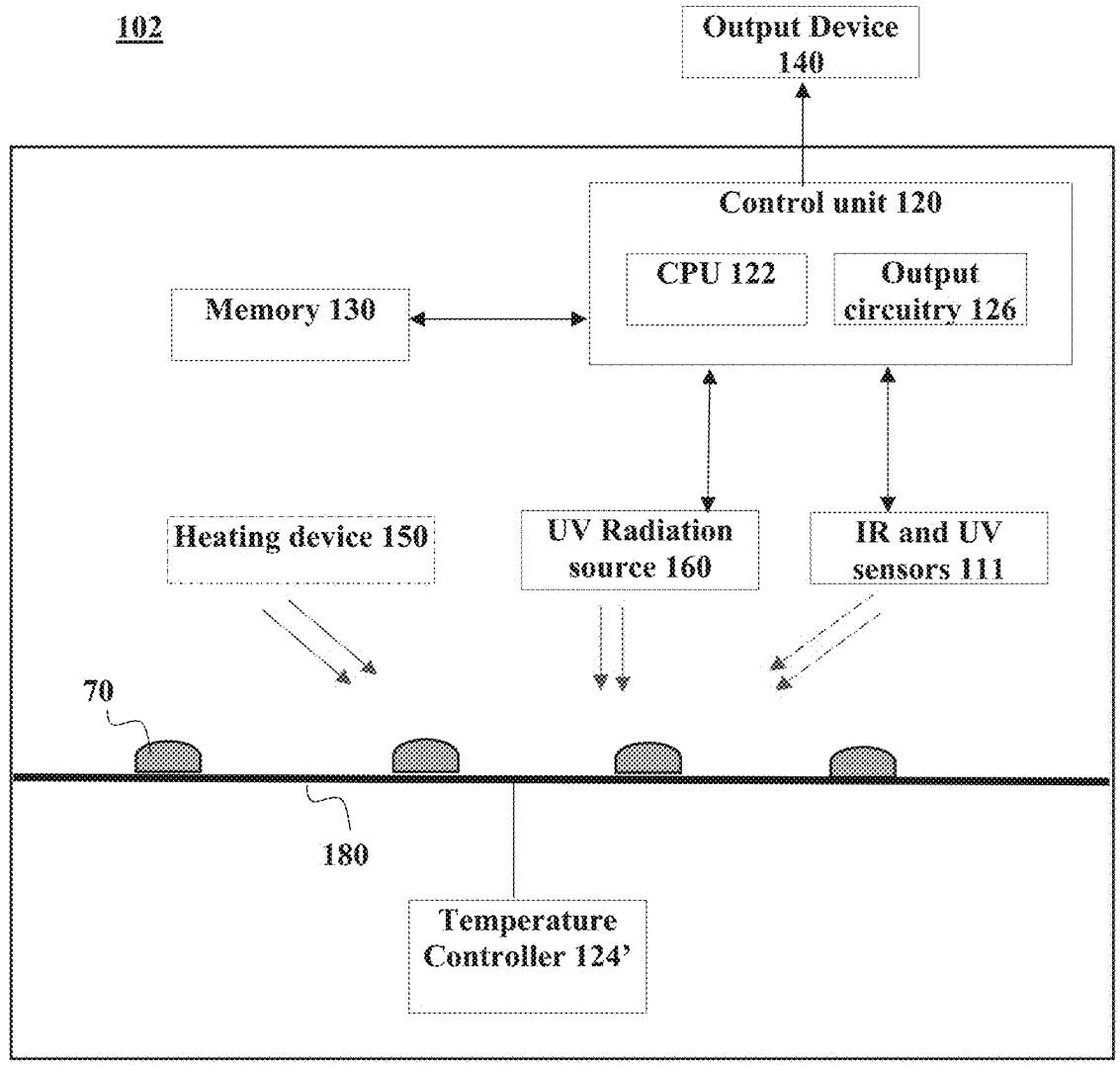
FIG. 2 schematically illustrates an apparatus for analyzing a plurality of tested gemstone according to some embodiments of the present disclosure.

Reference is made to FIG. 2, schematically illustrating an System/apparatus 102 for analyzing a plurality of tested gemstones, generally designated 70, according to some embodiments of the present disclosure. The System/apparatus 102 can be provided with a housing 170 including a replaceable/insertable support structure 180 (e.g., a support plate) for holding one or more tested gemstones 70 thereon.

The support element 180 may be configured, in some embodiments, as a heating element for heating the tested gemstones 70. The support plate 180 can for example be electrically heated and/or adapted to stream heated liquid therethrough, e.g., via one or more channels adapted for streaming the heated liquid therethrough from a heated liquid source (not shown). Temperature controller 124' can be operatively coupled to the support plate 180 for controlled heating thereof. Optionally, the support plate 180 may be equipped with one or more temperature sensors for measuring temperature of the gemstones 70 and generate measured data indicative thereof. The measured data can be communicated to the temperature controller 124' for adjusting temperature of the support plate 180 and/or the gemstones 70 e.g., until a desired temperature of the support plate 180 and/or gemstones 70 is achieved.

The temperature of the tested gemstones may be changed in accordance with various temperature variation schemes/profiles. For instance, the temperature may gradually increase and then gradually decrease to allow the gemstones to cool down. At least one IR image may be captured when the temperature is increasing and/or when the temperature is decreasing.

It should be noted that when the gemstones are heated at a certain temperature some classes/types of gemstones may not be distinguishable from other classes due to similar IR response which may result in a similar classification descriptor. Therefore, when gradually changing (e.g., gradually increasing) the temperature, such gemstones can exhibit different IR response and therefore may be more accurately classified. Additionally, after being heated, the gemstones can be gradually cooled down and images may be captured to thereby allow better classification of the gemstones and distinguishing between the different classes. In some cases, gradual increase in temperature while capturing IR images may yield a more accurate classification as compared to doing so at the cooling stage; or vice versa. It is possible also to do both, namely capture images while heating and, also while cooling. For example for CVD, HPHT and Zirconia, capturing images at single defined temperature is sufficient to classify them.

Figure 3:
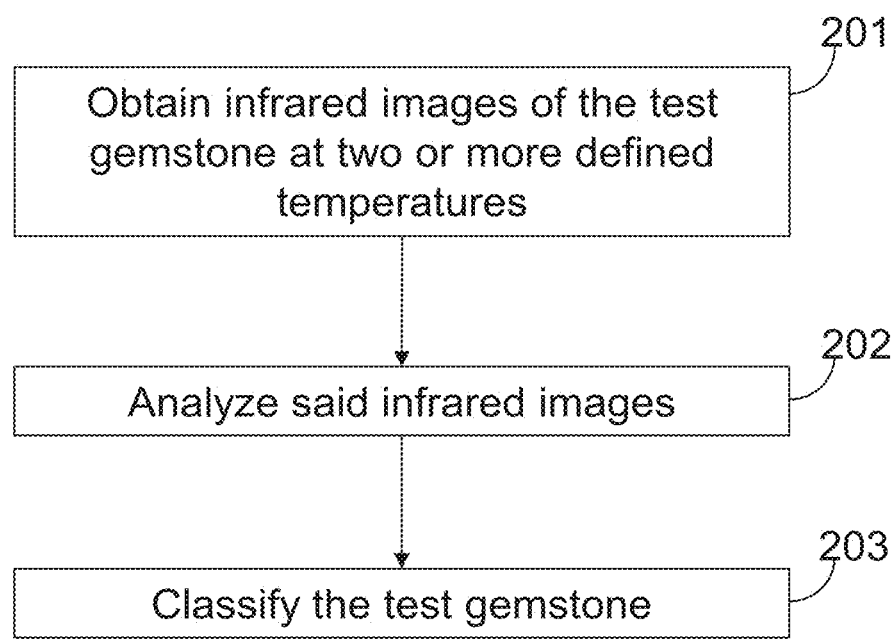
FIG. 3 is a flow diagram describing a method for analyzing the tested gemstone, according to some embodiments of the present disclosure.

The control unit 120 is configured for receiving and analyzing at least one infrared image for each of the defined temperatures (generally one or more) to obtain a respective classification descriptor for each of the one or more tested gemstones. In particular, each respective classification descriptor is assigned to the gemstone it is associated with. This way each of the one or more gemstones is analyzed and classified. Reference is made to FIG. 3, which is a flow diagram describing the method for analyzing the tested gemstone, according to some embodiments of the present disclosure. The steps of the method of FIG. 3 may be implemented by system/apparatus 100 of FIG. 1A (as described herein above).

In step 201, IR images of the tested gemstone may be captured at one or more defined temperatures (e.g., by sensor 110 described hereinabove). The temperature of the tested gemstone may be changed in a controlled manner (e.g., by controller 124 controlling temperature control unit 150 described hereinabove). While the temperature of the tested gemstone is being changed in a controlled manner, IR images of the tested gemstone may be at one or more defined temperatures. The temperature of the tested gemstone may be changed by heating the tested gemstone. The temperature of the tested gemstone may be changed by permitting the tested gemstone to cool. At least one IR image of the tested gemstone may be recorded for at least one temperature of the one or more defined temperatures (e.g., by processor 122). The IR images may be recorded in memory (e.g., memory 130 described hereinabove).

In step 202, said IR images are analyzed (e.g., by processor 122). Said IR images may be compared to reference IR images of gemstones belonging to a defined class. A measure of correlation of said IR images to said reference IR images is determined. Said measure of correlation may be indicative of the number of defined features shared between said IR images and said reference IR images (e.g., as described hereinabove).

In step 203, the tested gemstone is classified (e.g., by processor 122). The tested gemstone may be determined to belong to the defined class based on said measure of correlation indicating that the number of defined features shared between said IR images and said reference IR images exceeds the defined threshold. The defined threshold may be determined by a machine learning model trained on said reference IR images.

Figure 4:
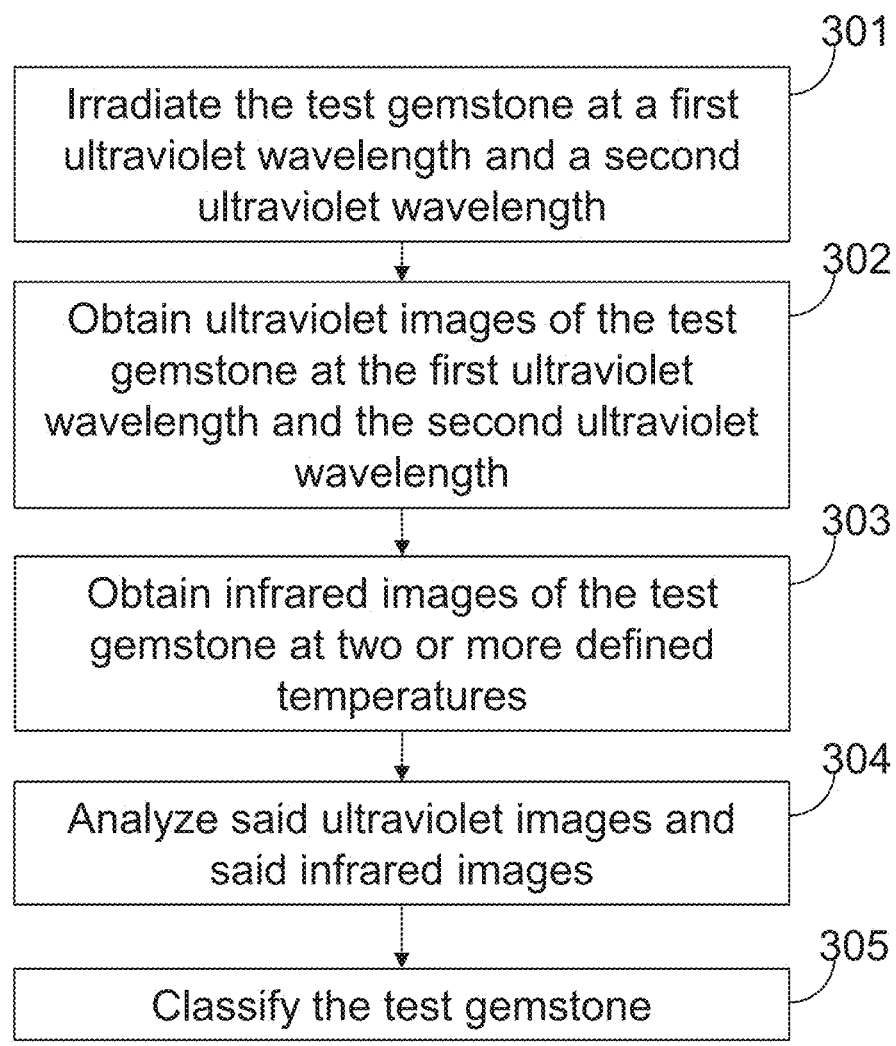
FIG. 4 is a flow diagram describing the method for analyzing a tested gemstone using the apparatus of FIG. 1B or FIG. 2, according to some embodiments of the present disclosure.

Reference is made to FIG. 4, which is a flow diagram describing the method for analyzing a tested gemstone using the system/apparatus of FIG. 1B or FIG. 2, according to some embodiments of the present disclosure.

In step 301, the tested gemstone is irradiated at by a UV radiation, at one or more UV wavelengths (e.g., by radiation source 150).

In step 302, UV images of the tested gemstone are captured (e.g., by sensor 111 as described hereinabove). The UV images may be recorded in memory (e.g., memory 130).

In step 303, IR images of the tested gemstone are captured at one or more defined temperatures (e.g., by sensor 110 as described hereinabove). The temperature of the tested gemstone may be changed in a controlled manner (e.g., by controller 124 as described hereinabove). While the temperature of the tested gemstone is being changed in a controlled manner, IR images of the tested gemstone may be recorded at one or more defined temperatures. The temperature of the tested gemstone may be changed by heating the tested gemstone. The temperature of the tested gemstone may be changed by permitting a heated tested gemstone to cool. At least one IR image of the tested gemstone may be recorded for each one of the one or more defined temperatures (e.g., by processor 122). The IR images may be recorded in memory (e.g., memory 130).

In step 304, said UV images and said IR images are analyzed (e.g., by processor 122). Said IR images may be compared to reference IR images of gemstones belonging to a defined class. A first measure of correlation of said IR images to said reference IR images is determined. Said first measure of correlation may be indicative of the number of defined features shared between said IR images and said reference IR images (e.g., as described hereinabove).

Said UV images may be compared to reference UV images of gemstones belonging to a defined class. A second measure of correlation of said UV images to said reference UV images is determined. Said second measure of correlation may be indicative of the number of defined features shared between said UV images and said reference UV images (e.g., as described hereinabove).

In step 305, the tested gemstone is classified (e.g., by processor 122). The tested gemstone may be determined to belong to the defined class based on said first measure of correlation and said second measure of correlation indicating that the number of defined features shared between said IR images and said reference IR images and the number of defined features shared between said UV images and said reference UV images exceed a first defined threshold and a second defined threshold, respectively. The first defined threshold and the second defined threshold may be determined by a machine learning model trained on said reference IR images and said reference UV images, respectively.

In some embodiments of the methods the order of the steps may be changed, for example steps 303-304 may preceded steps 301-302. In other embodiments, steps 301-302 may be carried out in parallel to 303-304.

The invention claimed is:

1. A method for classifying one or more tested gemstones, comprising:
   changing temperature of the one or more tested gemstones;
   capturing one or more infrared images of the one or more tested gemstone during the change of temperature of the one or more tested gemstones at one or more defined temperatures;

in a processer,
  receiving said one or more infrared images of the one or more tested gemstones,
  analyzing at least said one or more infrared images by
    comparing one or more of said infrared images associated with at least one certain temperature from the one or more defined temperatures to respective reference infrared images of gemstones belonging to a defined class and associated with said at least one certain temperature,
    and determining for each of the one or more tested gemstone whether said tested gemstone belongs to the defined class based on a first measure of correlation of said one or more infrared images associated with said at least one certain temperature from the one or more defined temperatures to said respective reference infrared images, and
  based on said analyzing, classifying each of the one or more tested gemstones to obtain a respective classification descriptor for each of the one or more tested gemstones, said respective classification descriptor for each of the one or more tested gemstones comprising an indication of or being based on said first measure of correlation; and
  outputting said classification descriptors.

2. The method of claim 1, for classifying each tested gemstone of the one or more the tested gemstones to the class to which it belongs.

3. The method of claim 1, comprising:
  irradiating the one or more tested gemstones with ultraviolet light at one or more ultraviolet wavelengths; and
  capturing one or more ultraviolet images of the one or more tested gemstones at each of the one or more ultraviolet wavelengths; and
  in the processor, receiving said one or more ultraviolet images of the one or more tested gemstones;
  wherein said step of analyzing at least said one or more infrared images further comprises analyzing said one or more ultraviolet images; and
  wherein said step of classifying each of the one or more tested gemstones to obtain the respective classification descriptor for each of the one or more tested gemstones is based on the analysis of said infrared images and of said ultraviolet images.

4. The method of claim 3, wherein said analyzing of said one or more infrared images and of said one or more ultraviolet images comprises:
  the comparing of the one or more of said infrared images associated with at least one certain temperature from the one or more defined temperatures to respective reference infrared images of gemstones belonging to a defined class and associated with said at least one certain temperature;
  comparing one or more of said ultraviolet images to respective reference ultraviolet images of gemstones belonging to the defined class to obtain a second measure of correlation; and
  determining for each of the one or more tested gemstones whether it belongs to the defined class based on
    said first measure of correlation of said one or more infrared images associated with said at least one certain temperature from the one or more defined temperatures to said respective reference infrared images, and
    said second measure of correlation;
  wherein said respective classification descriptor for each of the one or more tested gemstones comprises an indication of or being based on said first measure of correlation and on said second measure of correlation.

5. The method of claim 4, wherein the one or more ultraviolet images are discrete images, a video stream or a combination thereof.

6. A system for analyzing one or more tested gemstones, comprising:
  a temperature control unit configured for controlling heat of the one or more tested gemstones;
  one or more infrared sensors configured to obtain one or more infrared images of the one or more tested gemstones;
  a processor configured to receive and analyze at least the one or more infrared images to obtain a classification descriptor for each of the one or more tested gemstones, the analysis comprising
    comparing one or more of said infrared images associated with at least one certain temperature from the one or more defined temperatures to respective reference infrared images of gemstones belonging to a defined class and associated with said at least one certain temperature, and
    determining for each of the one or more tested gemstones whether said tested gemstone belongs to the defined class based on a first measure of correlation of said one or more infrared images associated with said at least one certain temperature from the one or more defined temperatures to said respective reference infrared images;
  an output utility to output said classification descriptors;
  wherein said respective classification descriptor for each of the one or more tested gemstones comprises an indication of or being based on said first measure of correlation.

7. The system of claim 6, comprising:
  a radiation source configured to irradiate the one or more tested gemstone with ultraviolet light at one or more ultraviolet wavelengths; and
  an ultraviolet sensor configured to capture one or more ultraviolet images of the tested gemstone at each of the one or more ultraviolet wavelengths;
  wherein the processor is further configured to receive and analyze said one or more ultraviolet images of the one or more tested gemstones to obtain the classification descriptor for each of the one or more tested gemstones such that the obtainment of the classification descriptor is also based on the analysis of said one or more ultraviolet images.

8. The system of claim 7, wherein the analysis of said one or more ultraviolet images comprises comparing one or more of said ultraviolet images to respective reference ultraviolet images of gemstones belonging to the defined class and associated with said at least one ultraviolet wavelength to obtain a second measure of correlation,
  wherein said determination for each of the one or more tested gemstone of whether it belongs to the defined class is further based on the second measure of correlation, and
  wherein said respective classification descriptor for each of the one or more tested gemstones comprises an indication of or being based on said first measure of correlation and on said second measure of correlation.

9. An apparatus for analyzing one or more tested gemstones, comprising:
  one or more infrared sensors configured to obtain one or more infrared images of the one or more tested gemstone;

a control unit comprising a temperature controller, the control unit comprising or being communicatively couplable to a processor;

the processor configured to receive and analyze at least the data representative of one or more infrared images captured by the one or more infrared sensors to obtain a classification descriptor for each of the one or more tested gemstones, the analysis comprising comparing one or more of said infrared images associated with at least one certain temperature from the one or more defined temperatures to respective reference infrared images of gemstones belonging to a defined class and associated with said at least one certain temperature, and determining determine for each of the one or more tested gemstones whether said tested gemstone belongs to the defined class based on a first measure of correlation of said one or more infrared images associated with said at least one certain temperature from the one or more defined temperatures to said respective reference infrared images;

wherein said respective classification descriptor for each of the one or more tested gemstones comprises an indication of or being based on said first measure of correlation.

10. The apparatus of claim 9, comprising:

a radiation source configured to irradiate the one or more tested gemstone with ultraviolet light at one or more ultraviolet wavelengths; and an ultraviolet sensor configured to capture one or more ultraviolet images of the tested gemstone at each of the one or more ultraviolet wavelengths; and wherein the processor is further configured to receive and analyze said one or more ultraviolet images of the one or more tested gemstones to obtain the classification descriptor for each of the one or more tested gemstones such that the obtainment of the classification descriptor is also based on the analysis of said one or more ultraviolet images.

11. The apparatus of claim 10, wherein the analysis of said one or more ultraviolet images comprises comparing one or more of said ultraviolet images to respective reference ultraviolet images of gemstones belonging to the defined class and associated with said at least one ultraviolet wavelength to obtain a second measure of correlation, wherein said determination for each of the one or more tested gemstone of whether it belongs to the defined class is further based on the second measure of correlation, and wherein said respective classification descriptor for each of the one or more tested gemstones comprises an indication of or being based on said first measure of correlation and on said second measure of correlation.

* * * * *